(12) United States Patent
Smith et al.

(10) Patent No.: US 7,450,991 B2
(45) Date of Patent: Nov. 11, 2008

(54) SYSTEMS AND METHODS USED TO RESERVE A CONSTANT BATTERY CAPACITY

(75) Inventors: Galen L. Smith, Allen, TX (US); John H. Erickson, Plano, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 574 days.

(21) Appl. No.: 11/138,120

(22) Filed: May 26, 2005

(65) Prior Publication Data

US 2005/0266301 A1     Dec. 1, 2005

Related U.S. Application Data

(60) Provisional application No. 60/575,466, filed on May 28, 2004.

(51) Int. Cl.
*A61N 1/00* (2006.01)
(52) U.S. Cl. ........................................................ 607/29
(58) Field of Classification Search .............. 607/27–34
See application file for complete search history.

(56) References Cited

U.S. PATENT DOCUMENTS

| 4,692,145 A | 9/1987 | Weyant et al. |
| 6,553,263 B1 * | 4/2003 | Meadows et al. ............. 607/61 |
| 2002/0115939 A1 | 8/2002 | Mulligan et al. |
| 2003/0065370 A1 | 4/2003 | Lebel et al. |

FOREIGN PATENT DOCUMENTS

| EP | 1 250 944 | 10/2002 |
| WO | WO 98/54811 | 12/1998 |

OTHER PUBLICATIONS

European Search Report issued for EP 05011432.1-2007 dated Nov. 16, 2005.

* cited by examiner

*Primary Examiner*—Scott M Getzow
(74) *Attorney, Agent, or Firm*—Christopher S. L. Crawford; Peter Lando; Melissa Acosta (57) ABSTRACT

Techniques are disclosed which provide a substantially constant battery reserve capacity with respect to therapeutic medical devices. Accordingly, a battery control system may be operable to maintain a substantially constant reserve capacity throughout the life of the battery. The battery reserve capacity activation threshold may be set and continuously or periodically updated so that a battery's remaining capacity equals the predetermined reserve capacity when the measured parameter reaches the activation threshold, thereby allowing a maximum amount of a battery's total capacity to be employed for therapeutic use and reserve only that portion of that capacity determined to provide for a desired level and/or period of device function after reaching the reserve threshold.

15 Claims, 4 Drawing Sheets

SYSTEMS AND METHODS USED TO RESERVE A CONSTANT BATTERY CAPACITY

CROSS-REFERENCE TO RELATED APPLICATIONS

The present application claims priority to U.S. Provisional Patent Application Ser. No. 60/575,466, entitled "SYSTEMS AND METHODS USED TO RESERVE A CONSTANT BATTERY CAPACITY," filed May 28, 2004, the disclosure of which is hereby incorporated herein by reference. The present application is related to commonly assigned U.S. Provisional Patent Application Ser. No. 60/568,384 entitled "MULTI-PROGRAMMABLE TRIAL STIMULATOR," filed May 5, 2004, the disclosure of which is incorporated herein by reference.

TECHNICAL FIELD

The present invention relates generally to systems relying upon battery power, and more particularly to systems and methods for managing battery power to provide a constant reserve battery capacity.

BACKGROUND OF THE INVENTION

Electrically powered therapeutic medical devices are in widespread use, and an increasing number of these devices use battery power as a primary or auxiliary power source. Therapeutic medical devices include such equipment as electronic stimulation systems, which may be used to control pain by nerve stimulation. As a specific example, spinal cord stimulation (SCS) is a technique that has been prescribed since the 1960s for pain management, and uses an electronic stimulation system. When deployed, SCS systems generally feature a pulse generator coupled to one or more percutaneous leads having a plurality of electrodes disposed in an area in which neurostimulation is desired.

The pulse generator of an electronic stimulation system may be provided in various configurations, such as a totally implanted pulse generator (IPG) or a radio frequency (RF) system. A typical IPG configuration comprises a surgically implanted, internally-powered pulse generator and multi-electrode lead, while an RF system configuration often comprises a surgically implanted, passive receiver and a transmitter which is worn externally. Electronic stimulation systems may also utilize implanted electrodes with external pulse generators and controllers.

A battery, when fully charged at 100 percent of its total capacity, is able to deliver a finite amount of power. After a period of discharge, a battery's remaining capacity will be at some lower percentage of its total capacity. Many battery-powered therapeutic devices, such as electronic stimulation systems, typically cannot have battery power depleted below a certain percentage of total capacity before the device's processor and the device itself become nonfunctional. Also, for devices employing memory and/or processors, if power is completely drained from the battery power source, various system settings may be lost if minimum operational power is not maintained.

For some battery systems, a battery's output voltage can be used to estimate the remaining capacity of a battery relative to its total capacity when fully charged. Some existing battery-powered medical devices utilize this relationship, and set operational thresholds based on a fixed output voltage of the battery. However, in a rechargeable battery, total battery capacity decreases as the number of discharge and recharge cycles increases. Likewise, the total battery capacity generally also decreases with the battery age. Because the total battery capacity of batteries decreases with age and/or charge history, using a fixed voltage-level to reserve capacity requires setting the fixed level high enough to provide the desired reserve capacity at the end of the battery's life cycle. Therefore, using such a fixed level to reserve capacity will require that a larger-than-required capacity be reserved when the device is new than when it is near its end of life.

The foregoing fixed voltage-level method is inefficient because it reserves energy in excess of minimum operational power that cannot be used for a device's function during normal operating periods. Accordingly, there exists a need for battery-powered medical devices that better calculate and take action according to a battery's capacity.

While therapeutic medical devices such as pacemakers have employed rechargeable batteries in the past, these devices, as well as electronic stimulation systems such as neurostimulators, would benefit from inventions that improve the determination of a battery's total capacity and the implementation of a battery's reserve capacity. Improvements that would allow an electronic stimulation system more useable battery capacity early in a battery's life, yet provide a safe reserve capacity at the end of a battery's usable life are therefore desirable.

BRIEF SUMMARY OF THE INVENTION

The present invention is directed to systems and methods which provide a substantially constant battery reserve capacity with respect to therapeutic medical devices. In some embodiments, a battery control system may be operable to maintain a substantially constant reserve capacity throughout the life of the battery. A battery's reserve capacity is a portion of a battery's total capacity. A battery-powered device according to an embodiment of the present invention may take some action once a battery's remaining capacity reaches its reserve capacity. Embodiments of the invention may comprise a processor and software that may be used to reserve a constant battery capacity, and the software may be written in the processor's source code. The battery reserve capacity may be used to power, for example, an electronic stimulation system, particularly after stimulation is purposely or automatically turned off or reduced, so that a user can recharge the battery or perform other tasks.

Embodiments of the present invention may take certain actions once an activation threshold is reached for a measured parameter such as battery output voltage, output current, recharge voltage, recharge current, discharge rate, recharge rate, number of recharge cycles, age, et cetera, as well as combinations thereof. In these embodiments, the activation threshold may be set and continuously or periodically updated so that a battery's remaining capacity equals the predetermined reserve capacity when the measured parameter reaches the activation threshold. Once the activation threshold is reached, an action may be performed. The action may comprise, for example, turning off therapy, reducing the quantity or quality of delivered therapy, notifying a user, switching to a low-power mode, switching to an alternate mode of operation or therapeutic operation and/or the like. In other embodiments, the action contemplated may be the generation of a control signal for activating a device function. Embodiments may utilize single activation thresholds or may have multiple activation thresholds. Each activation threshold may have single or multiple actions to be performed, and embodiments may generate single or multiple control signals for each activation threshold.

A benefit of embodiments of the invention is that they allow a maximum amount of a battery's total capacity to be employed for therapeutic use and reserve only that portion of that capacity determined to provide for a desired level and/or period of device function after reaching the reserve threshold. Embodiments of the invention may calculate a battery's present total capacity as a means to reserve a constant battery reserve capacity. Then an activation threshold for a measurable battery parameter, such as charging resistance, recharge or discharge rate, battery age, battery temperature, et cetera, is chosen, such that when an activation threshold is reached for that parameter, the battery's remaining capacity is equal to the constant reserve capacity. This reserve capacity may be held constant or substantially constant throughout the battery's life to ensure that, for example, an electronic stimulator system powered by this battery has a constant reserve capacity that can be used to power the system after the normal operational battery capacity used to produce stimulation has been exhausted, and allow the device to remain powered sufficiently to respond to a charger and/or give the patient a constant amount of time to recharge the battery. A reserve capacity may be selected based upon various criteria, such as a number of days of normal operation remaining or a number of days of retention of an operating program, and the actual amount of battery capacity in the reserve determined based upon operating parameters, such as battery current usage associated with a program being executed. Embodiments of the invention can also be used to avoid the condition where a rechargeable battery's voltage drops too low to respond to a charger and damages the battery.

In some embodiments of the present invention, the change in a battery's output voltage over a given time during discharge from a known output current may be used to reserve a constant battery reserve capacity. In embodiments using rechargeable batteries, a battery's reserve capacity may also be calculated during a recharge cycle by measuring the change in the battery output voltage over time for a known charging current. In other embodiments using rechargeable batteries, a battery's charging resistance may be used to calculate the reserve capacity of the battery. Some embodiments may utilize single or multiple batteries. Batteries used by embodiments of the present invention include rechargeable and non-rechargeable batteries.

Preferred embodiments of the present invention may include an implantable electronic stimulation system using a rechargeable battery. In one embodiment, a battery control system may calculate a battery's reserve capacity by employing a software program and a processor to estimate the reserve capacity using a table residing in memory. The battery's reserve capacity may be calculated to provide a selected and/or selectable amount of reserve capacity, such as a particular number of days of operation using a particular stimulation program, a selected reserve energy level (e.g., X milliamp hours), a particular number of days before continued operation results in damage to the battery, a particular number of days minimum operations (e.g., "sleep" mode) will retain control program settings, etcetera. A table may be set so that at the beginning of a battery's life, a device may have an activation threshold based on output voltage that would be much lower on the voltage curve relating to a given battery reserve capacity, and at the end of life that voltage point would be raised to a higher value equating to the same reserve capacity.

In another embodiment, a programmable voltage comparator may be used, comprising, for example, a voltage divider where the resistance in one circuit branch could be varied such that over the life of the battery the resistance value would change. Changing the resistance value would allow an action to be taken once battery remaining capacity reached reserve capacity. In other embodiments, the comparator could produce a control signal once reserve capacity is reached.

A multiple activation threshold feature may be provided in some embodiments. Embodiments including this feature may have, for example, one activation threshold for a measurable parameter set establishing a reserve capacity having been reached. In some embodiments, a control signal may be generated once the system reached that threshold, and provide, for example, a warning for the battery to be recharged. A second activation threshold establishing that the reserve capacity has been depleted to a predetermined extent may be included, for example, where the therapeutic device reduces the quantity or quality of therapy, thus reserving battery capacity to maintain memory and other functions for a much longer period of time. Multiple activation thresholds may be set for the same measurable parameter or for different measurable parameters in some embodiments.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

Figure 1:
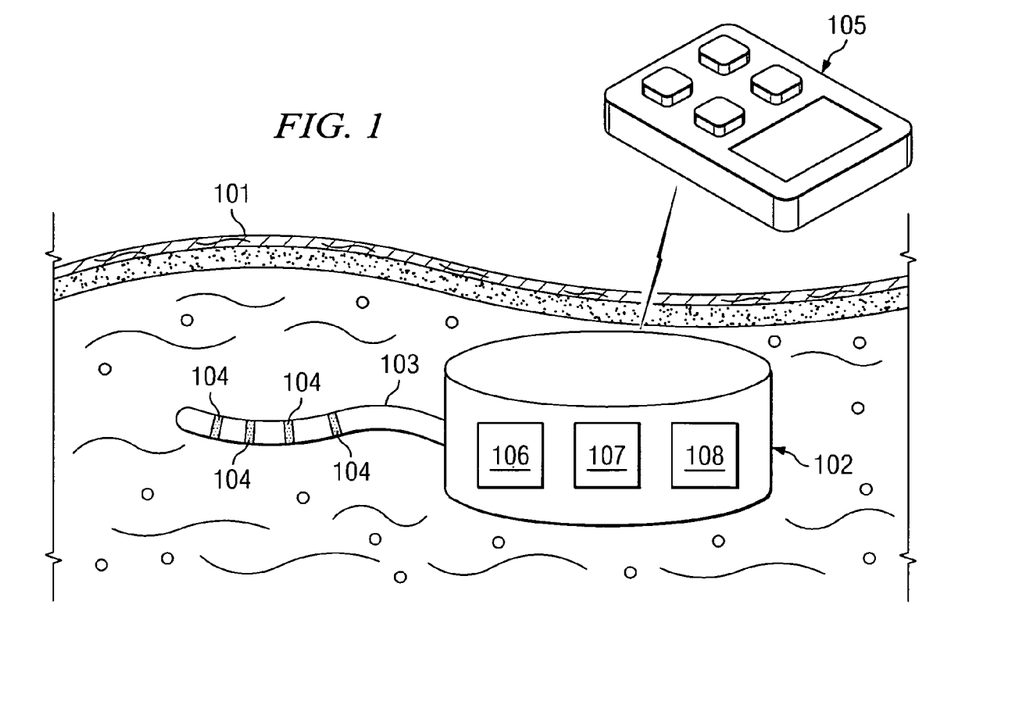
FIG. 1 shows a diagram of an electronic stimulation system according to a preferred embodiment of the present invention.

FIG. 1 shows an electronic stimulation system adapted according to a preferred embodiment of the present invention. As shown in FIG. 1, an exemplary electronic stimulation system includes a pulse generating portion, shown here within pulse generator housing 102, and a stimulation delivery portion, shown here including electrodes 104. In the illustrated embodiment, pulse generator housing 102 may be implantable and inserted surgically beneath the skin 101 of a patient. Electrodes 104 may be coupled to a pulse generator 107 located inside implantable pulse generator housing 102 via lead 103. Electrodes 104 are located in an area selected to receive electrical stimulation. In some embodiments, more or less electrodes 104 and/or leads 103 than shown may be used. Electrodes 104 and portions of lead 103 in the illustrated embodiment are electrically conductive and capable of delivering an electrical pulse to the selected area.

Embodiments configured other than illustrated in FIG. 1 may be utilized according to the present invention. For example, a non-implantable pulse generator may be used and worn, for instance, in a location convenient for placement of electrodes 104. Other embodiments may comprise a microstimulator, wherein a pulse generating portion and a stimulation delivery portion are disposed in a contiguous housing.

Interface 105 may be in communication with components within housing 102, such as pulse generator 107, to provide control thereof and/or to receive information, signals, et cetera, therefrom. Interface 105 may be provided such communication using wires, or may use wireless communication methods.

Pulse generator 107 may be connected electrically to battery 106 and to electrodes 104. Battery reserve capacity may be calculated by battery control system 108 which may be electrically connected to battery 106. In some embodiments, battery control system 108 may generate a control signal, which may be used by the system to perform an action according to the generated signal. In other embodiments, battery control system 108 may also be coupled to pulse generator 107.

In a preferred embodiment, battery control system 108 is operable to maintain a substantially constant reserve capacity throughout the life of battery 106. Periodic adjustments of a battery's reserve capacity based on factors such as service life, recharge cycles, et cetera, may be used to keep a substantially constant reserve capacity. Periodic adjustments may be made at constant time periods, such as every week, month, or year, or may be event-determined and made, for example, when a battery is recharged or discharged. In some embodiments, adjustments may be random or infrequent. Battery reserve capacity may be set in embodiments of the invention by first determining the battery total capacity using one or more methods, alone or in combination, sequentially or in parallel. In other embodiments, a battery's total capacity may not be determined but rather information indicative of a battery's total capacity may be used. Methods used to determine the total capacity of battery 106 or which are otherwise indicative of a battery's total capacity may include: measuring the change or rate of change in battery output voltage during the application of a known total charge, measuring the change or rate of change in battery output voltage based on total power discharged, measuring the change of a battery's charging resistance by measuring the change in an applied charge voltage over time, correlating one or more measurements of measurable parameters, such as a battery's age or charging resistance, to a table of total capacities, and using a voltage comparator to determine total capacity. In some embodiments, once the total battery capacity has been determined, an activation threshold for a measurable battery parameter, such as output voltage, may be chosen, such that when an activation threshold is reached for that parameter, the battery's remaining capacity is equal to a desired constant reserve capacity. These methods are described in further detail below.

In operation, pulse generator 107 uses power from battery 106 to generate an electrical pulse that is transmitted to patient via lead 103 and electrodes 104. Electrical stimulation of dermatomes in some embodiments may result in perceived parathesia by the patient. The voltage and current characteristics of the electrical pulse generated by the system may vary in different embodiments of the present invention. Interface 105 may monitor various operational parameters of the system, or may be used to program the system. Interface 105 may respond to a control signal generated by battery control system 108.

Figure 2:
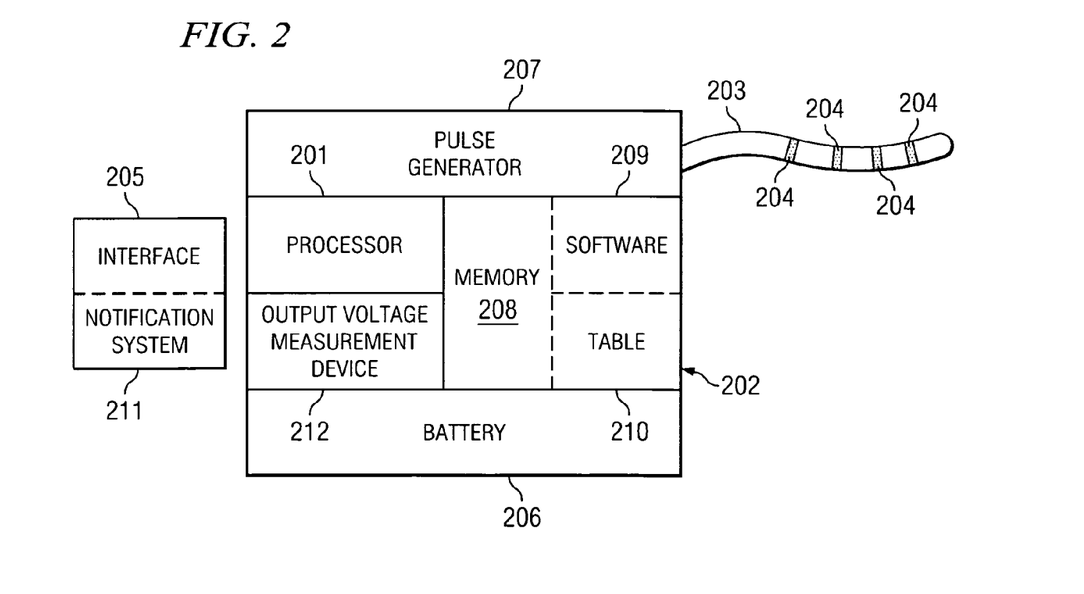
FIG. 2 is a block diagram of an electronic stimulation system according to an embodiment of the present invention.

Referring now to FIG. 2, a block diagram of an electronic stimulation system according to an embodiment of the present invention is shown. Pulse generator housing 202 may contain pulse generator 207 which may deliver electrical impulses through electrically conductive lead 203 to electrodes 204. In other embodiments, more than one lead 203 and/or more or less electrodes 204 may be used with pulse generator 207. Pulse generator 207 may be electrically connected to battery 206 either directly or via processor 201 or other intermediate electronic components. Pulse generator housing 202, interface 205, battery 206, and pulse generator 207 correspond to the elements of the same name in FIG. 1 numbered 102, 105, 106, and 107.

Battery 206 may be either single-use or rechargeable and may employ various electrochemical reactions for the production of electrical current. For example, battery 206 may be a zinc-carbon dry cell, an alkaline zinc-manganese dioxide battery, or a silver oxide battery. In a preferred embodiment, battery 206 is a rechargeable lithium ion battery. In some embodiments, battery 206 may employ non-chemical methods such as nuclear decay to generate electrical current. Battery 206 of embodiments may comprise a rechargeable circuit element, such as a capacitor. Battery 206 may also generate electricity or recharge itself using bio-kinetic energy from the movement of the user or patient, and/or may use bioelectric energy.

Some embodiments of the present invention may include a battery output voltage measurement device 212. This can be an instrument such as a digital device analyzer (DDA) or other electronic circuitry that sends processor 201 a signal corresponding to battery 206 output voltage. Signals provided to processor 201 corresponding to battery 206 output voltage need not be a direct measurement of the output voltage of battery 206. For example, battery output voltage measurement device 212 may comprise an analog to digital converter providing a digital signal indicative of whether the output voltage is above or below one or more threshold voltages, indicative of the output voltage level to a predetermined level of resolution, etcetera.

Processor 201 may be connected to memory 208, in which software 209 and table 210 reside. Embodiments of processor 201 comprise a microprocessor, a state machine, or other processing circuitry as known in the art.

In some embodiments of the present invention using software 209 and table 210, the reserve capacity of battery 206 is calculated by having processor 201 compare battery output voltage (relayed from battery output voltage measurement device 212) to table 210. Table 210 may include several variables for correlating battery output voltage to battery reserve capacity and/or total capacity. These variables may include, for example, battery age, battery usage characteristics, battery charging history, battery temperature, and/or other factors that are determined to influence the correlation between battery total capacity and measured battery output voltage. Table 210 may include, for example, seven different reserve capacity voltage activation thresholds for a battery with an anticipated lifetime of seven years. As the battery ages, a different reserve capacity activation threshold may be used from the table for each year the battery is in service. In different embodiments, other time periods, such as months or weeks, may be used. In yet other embodiments of the present invention, measurable parameters in addition to or in the alternative to age may be used to correlate battery output voltage to battery reserve capacity. These parameters may include, for example, the number of battery recharge and discharge cycles, charging resistance, charging voltage and/or current, discharge voltage and/or current, and/or temperature. Software 209 may compare measured battery output voltage to table 210 in other embodiments.

In some embodiments, if the measured battery output voltage is at a reserve capacity activation threshold, software 209 may activate a notification system 211 notifying a user, for example, that battery 206 should be recharged or replaced, or that some other action should be taken. Notification system 211 may reside in an interface 205 which may be integral to or separate from pulse generator housing 202. In a preferred embodiment, notification system 211 resides in an interface 205 separate from pulse generator housing 202. Interface 205 may be coupled to software 209 and/or pulse generator housing 202 using wired (e.g., universal serial bus (USB), Ethernet, fiber optic, etcetera) links and/or wireless links (e.g., infrared, bluetooth, Institute of Electrical and Electronic Engineers (IEEE) 802.11 wireless communication, etcetera).

As another example, in IPG systems according to embodiments of the present invention that utilize rechargeable batteries, it may be desirable that the system takes action once its battery's remaining capacity reaches a predetermined level. This action should occur early enough so that a patient has ample time to recharge or change the battery before the battery capacity is exhausted and the device must shut down or enter a power-saving mode. Predicate IPG devices used a fixed voltage to set the reserve capacity. In these systems, to insure, for example, 30 days reserve at the end of the life of the battery, a voltage threshold may be set at 3 volts. However, for a brand new battery, this 3 volt threshold would result in a reserve capable of operation in excess of the 30 day reserve period, e.g., 120 days of reserve capacity, at the expense of reduced normal operation capacity.

One advantage to embodiments of the present invention is that by maintaining a constant battery reserve capacity during the lifetime of a battery powering a therapeutic medical device, approximately forty percent more power may be provided at the beginning of battery life. Therefore, a patient would have forty percent more energy available for therapeutic use at the beginning of a battery's lifetime while still being ensured of sufficient reserve capacity to reliably facilitate activities such as reduced stimulation and/or allowing a period for recharge even at the end of a battery's life.

Figure 3:
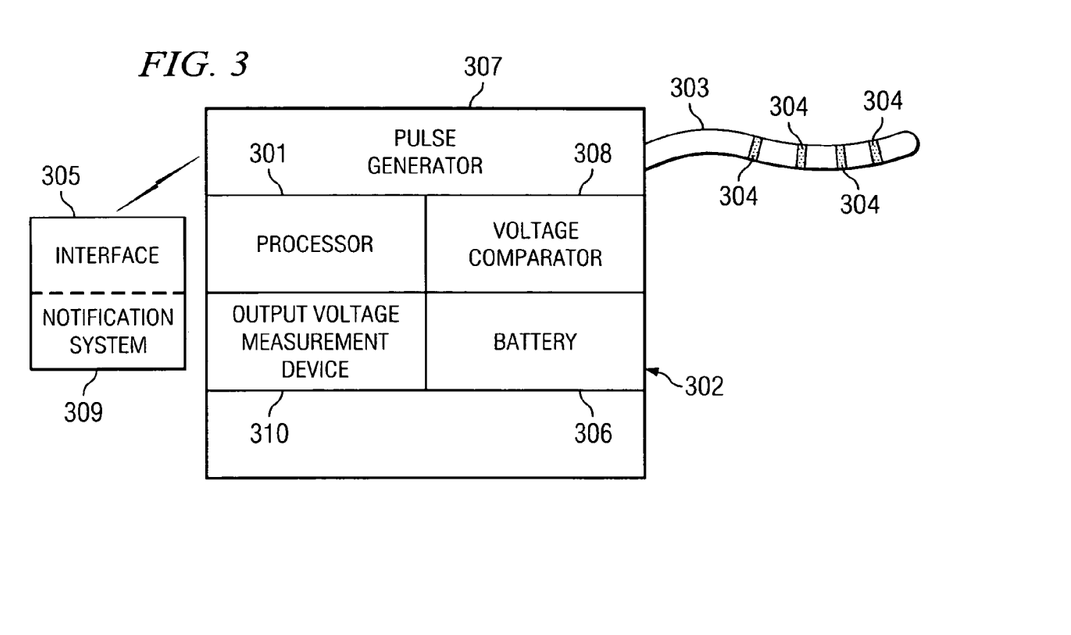
FIG. 3 is a block diagram of an embodiment utilizing a hardware-based system for determining battery reserve capacity.

FIG. 3 shows an embodiment utilizing a hardware-based system for determining battery 306 reserve capacity. FIG. 3 may correspond to the pulse generator housing and components shown in FIG. 1 and designated by numbers 102, 106, 107, and 108. In this embodiment, pulse generator housing 302 may contain a voltage comparator system 308 that is electrically coupled to processor 301 and battery output voltage measurement device 310. Voltage comparator system 308 may be a voltage control or resistant control hardware comparator, may be a programmable voltage comparator and/or the like. Voltage comparator system 308 may constitute a voltage divider where the resistance in one circuit branch of the voltage divider may be varied such that over the life of battery 306 the activation threshold of the system may change. In such an embodiment, voltage comparator system 308 and voltage measurement device 310 essentially comprise an analog to digital converter. Once the battery output voltage measured by battery output voltage measurement device 310 reaches the reserve capacity activation threshold, the voltage comparator system 308 may tell processor 301 to activate notification system 309 residing, in some embodiments, on interface 305.

Rather than providing voltage measurement and voltage comparator circuitry in addition to processor 301, embodiments of the invention may implement circuitry of processor 301, such as an analog to digital converter thereof, in providing output voltage measurement and/or threshold comparison. Additionally, circuitry of processor 301 may be used in confirming that the battery output voltage, or other measurable parameter, has reached a particular threshold.

Figure 4A:
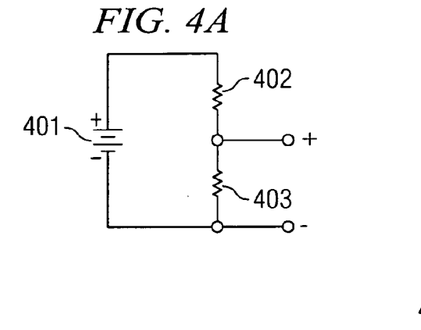
FIGS. 4A, 4B, and 4C show circuit schematics of voltage comparator systems using voltage divider circuits that may be present in some embodiments of the present invention.
Figure 4B:
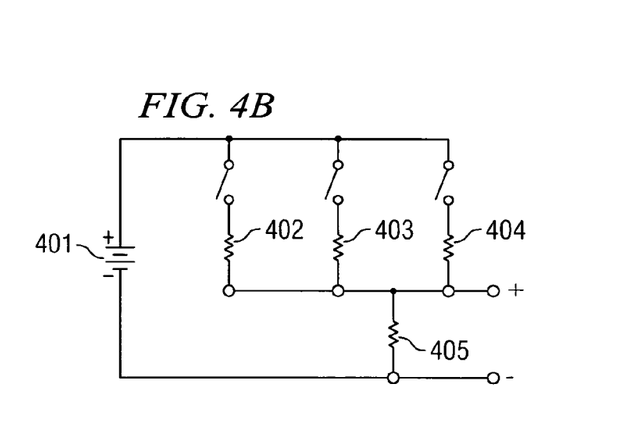
Figure 4C:
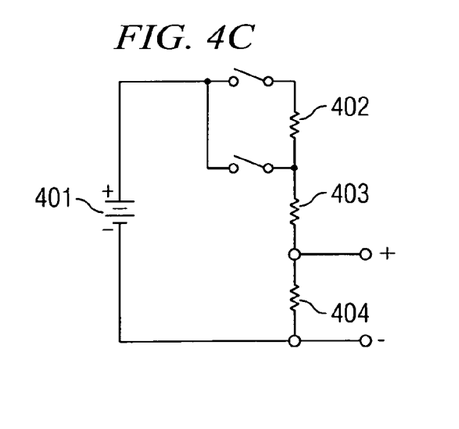

FIGS. 4A, 4B, and 4C show circuit schematics of voltage comparator systems using voltage divider circuits that may be present in some embodiments of the present invention. The illustrated systems may correspond to voltage comparator systems shown as 308 in FIG. 3. In FIG. 4A, battery 401 is connected to a voltage divider circuit comprised of resistors 402 and 403. In this embodiment, resistor 402 is variable or replaceable and may be changed during the operational life of battery 401 as in one of the techniques illustrated in FIGS. 4B and 4C, so that voltage divider circuit provides an appropriate control signal as battery reserve capacity reaches a desired point.

In FIG. 4B, a voltage comparator system schematic is shown that utilizes a battery 401 in connected to several switched resistors 402, 403, and 404. The number of switched resistors may vary in other embodiments. As battery 401 ages, the resistor selected from 402, 403, 404 may be changed so that voltage comparator system provides an appropriate control signal as battery reserve capacity reaches a desired point. Resistor 405 may be a permanent, non-switchable resistor in this embodiment.

In FIG. 4C, shows a voltage comparator system comprising battery 401 and several switched resistors 402, 403, and 404 wired in series. As battery 401 ages, the resistor selected from 402, 403, 404 may be changed so that voltage comparator system provides an appropriate control signal once battery remaining capacity equals battery reserve capacity.

Figure 5:
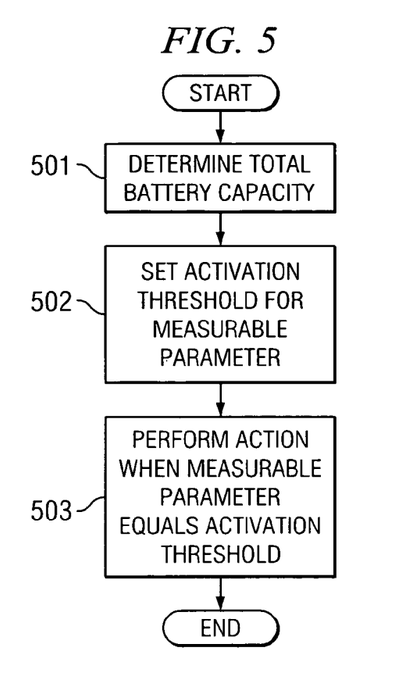
FIG. 5 is a flow diagram of a method according to an embodiment of the present invention.

FIG. 5 is a flow chart of a method according to an embodiment of the present invention. In step 501, the total battery capacity of a therapeutic medical device's battery may be determined. In some embodiments, more than one battery may be used in a device, so multiple determinations may be implemented for multi-battery systems. Multiple determinations for each individual battery's total capacity may also be made. A battery's total capacity may be determined using one or more of several methods. These methods may include those methods described briefly in FIG. 1 and described in further detail in FIGS. 6-8. In some embodiments, the total capacity of the battery may be estimated. In yet other embodiments, the total capacity of the battery may not be measured, but instead information indicative of the total capacity of the battery may be used to maintain a constant reserve capacity.

Once the total capacity of a battery has been determined, a reserve capacity activation threshold for a measurable parameter may be set in step 502. In preferred embodiments, the reserve capacity activation threshold is set so that once a measurable parameter reaches the reserve capacity activation threshold, a battery's remaining capacity equals a desired constant reserve capacity, such as may correspond to a minimum period of continued operation. The measurable parameter may vary in other embodiments include such parameters as charging resistance, charging voltage and/or current, discharge voltage and/or current, and/or battery age. In step 503, an action or actions may be performed by a device. Action may comprise, for example, entering a low-power mode, notifying a user, ceasing operations, or reducing the quantity or quality of delivered therapy.

Figure 6:
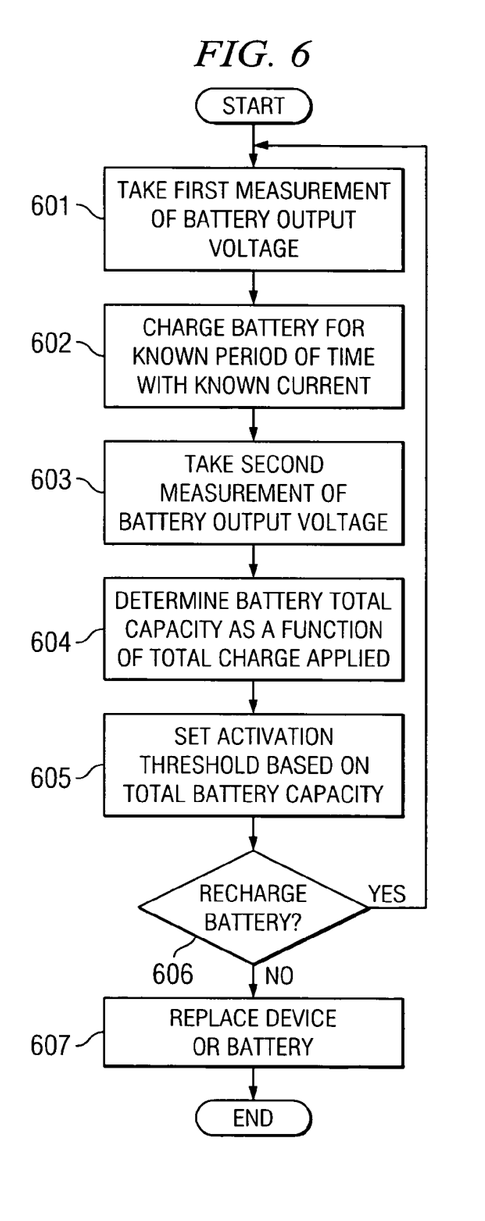
FIG. 6 shows a flow diagram of a method according to an embodiment of the invention that uses at least one rechargeable battery.

FIG. 6 shows a flow chart of a method according to an embodiment of the invention that uses at least one rechargeable battery. In step 601, a first output voltage measurement of a rechargeable battery used in an embodiment may be taken. In step 602, a rechargeable battery used to power an electronic stimulation system is recharged using a known charge current. The time during which the charge current is applied is tracked. The charge current may be constant, or may vary in some embodiments. In step 603, the rechargeable battery's output voltage is measured for a second time by a battery output voltage measuring device. In step 604, the battery's total capacity is determined as a function of the change in the battery output voltage from the total charge applied. Total charge applied may be calculated as a function of applied charge current and the time during which current is applied to a battery. If a variable charge current is used, the total charge applied may be calculated by integrating the charge current over time. If either constant or variable charge current is applied to the battery, the battery's total capacity is calculated based on the battery output voltage change resulting from the total charge applied. In step 605, the battery total capacity calculated in step 604 is used to set a reserve capacity activation threshold. A reserve capacity activation threshold in some embodiments may be a certain value for a measurable parameter such as battery output voltage that corresponding to a constant battery reserve capacity. The reserve capacity activation threshold set may provide an electronic stimulation system with a certain amount of operational time. In some embodiments, once the reserve capacity activation threshold is reached, an electronic stimulation system may activate a notification system indicating that a battery should be recharged. In other embodiments, multiple reserve capacity activation thresholds may be used corresponding, for example, to a first notification event that instructs a user to recharge a battery and a second event that results in the electronic stimulation system entering a low-power mode to preserve programming instructions. In step 606 a battery may or may not be recharged, depending on the age of the battery. If the battery is still within its operational lifetime, it may be recharged. However, if the battery is outside of an acceptable age, the battery or electronic stimulation system may be replaced in step 607.

As an example of an embodiment of the invention using a rechargeable battery, a lithium ion battery is used. A lithium ion battery's discharge voltage under a constant current load is almost linear from 4.2 v to 3.0 v, and therefore the percentage of capacity remaining at any point during discharge is a function of the battery voltage. However, the slope of the battery curve generated by graphing a lithium ion battery's discharge voltage against power discharged changes over the battery life. Therefore, determining the battery reserve capacity using the discharge voltage alone is not sufficiently accurate to establish a constant reserve capacity. Lithium ion batteries also have the characteristic that if discharged below 2.5 v the battery capacity will degrade substantially. Therefore, it is desirable that an electronic stimulation system using a lithium ion battery not be discharged below 2.5 v, and a minimum battery output voltage of 2.85 v may be selected to preserve a margin of safety. In this example of the present invention, when the lithium ion battery reaches a predetermined output voltage threshold, or reserve capacity activation threshold, the electronic stimulation system may discontinue stimulation and go into a power-saving mode. During the period from the reserve capacity activation threshold and 2.85 v it is desirable for the system to remain powered for 30 days giving a patient substantial time under any circumstance to recharge the device. A reserve capacity activation threshold voltage, in this example, can be determined by the following formula:

Remaining Capacity×1.2 v+3.0 v=reserve capacity activation threshold voltage Battery Reserve Capacity The battery reserve capacity in the denominator of this formula may be determined using any of the methods disclosed herein.

Figure 7:
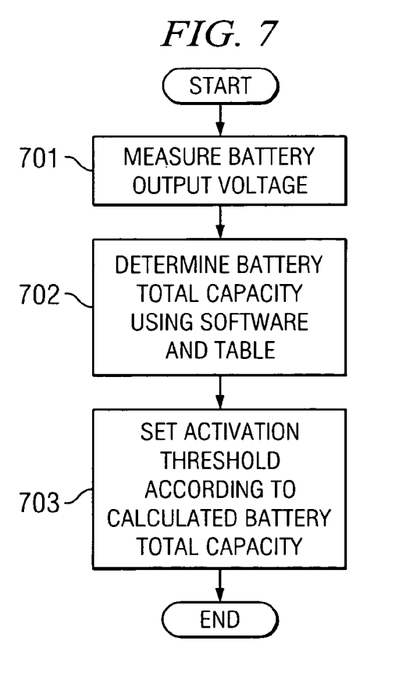
FIG. 7 shows a flow diagram of a method according to another embodiment of the present invention.

In FIG. 7, a flow diagram shows a method according to another embodiment of the present invention. In step 701, the output voltage from a therapeutic medical device's battery may be measured by, for example, a voltage measuring device. The measured output voltage may be compared by software to a table of parameters in step 702 and used to determine a battery's total capacity. In other embodiments, a table of parameters may include such parameters as battery age, number of battery discharge and recharge cycles, charging voltage and/or current, discharge current and/or voltage, battery temperature, and/or the like. In step 703, a reserve capacity activation threshold for a measurable parameter is set according to the determined total capacity of the battery. In this embodiment, once a reserve capacity activation threshold is reached for a measurable parameter, the battery's remaining capacity may equal a constant reserve capacity. This constant reserve capacity may be maintained in some embodiment throughout the lifetime of the battery.

In some embodiments, a battery's resistance to charging may be measured and used to determine a battery's reserve capacity. During the life of a rechargeable battery such as a lithium ion cell, the resistance to charging goes up as a battery ages. Therefore, the charging resistance can be used to determine a battery's reserve capacity activation threshold. In these embodiments, charging power and voltage applied to the battery is measured. As the battery's charging resistance increases with age, the charging voltage should drop if charging power is constant. As in other embodiments, once the battery's total capacity is determined, a reserve capacity activation threshold may be set based on the battery's output voltage that corresponds to a known amount of time left to continue normal electronic stimulator system operations.

Figure 8:
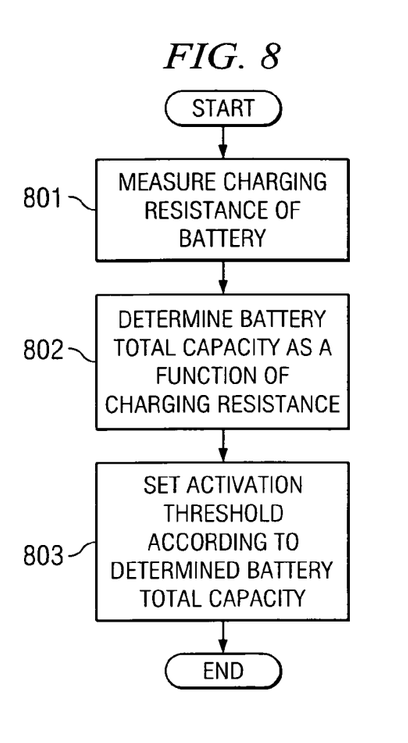
FIG. 8 shows a flow diagram of a method according to an embodiment of the present invention that uses a battery's charging resistance to set a constant reserve capacity.

In FIG. 8, a flow diagram shows a method according to an embodiment of the present invention that uses a battery's charging resistance to set a constant reserve capacity. In step 801, a battery's charging resistance may be measured. The measured charging resistance may be compared in some embodiments by software to a table of parameters in step 802 and used to determine a battery's total capacity. In step 803, a reserve capacity activation threshold for a measurable parameter is set according to the determined total capacity of the battery. In this embodiment, once a reserve capacity activation threshold is reached for a measurable parameter, the battery's remaining capacity may equal a constant reserve capacity. In some embodiments of this method, a battery used with the invention may not have a linear correlation between charging resistance and total capacity. In these embodiments, alternate methods disclosed here may be used to verify or to replace a method using charging resistance. Some methods of determining total capacity may produce more accurate results at different points during the lifetime of a battery used with embodiments of the invention, and may be selected for their accuracy.

In yet other embodiments of the invention, a battery's output voltage may be measured during use of the battery and the accompanying discharge of the battery's stored potential energy. The battery's total capacity may be extrapolated by measuring the change in output voltage of the battery resulting from a known amount of energy expended during use.

Figure 9:
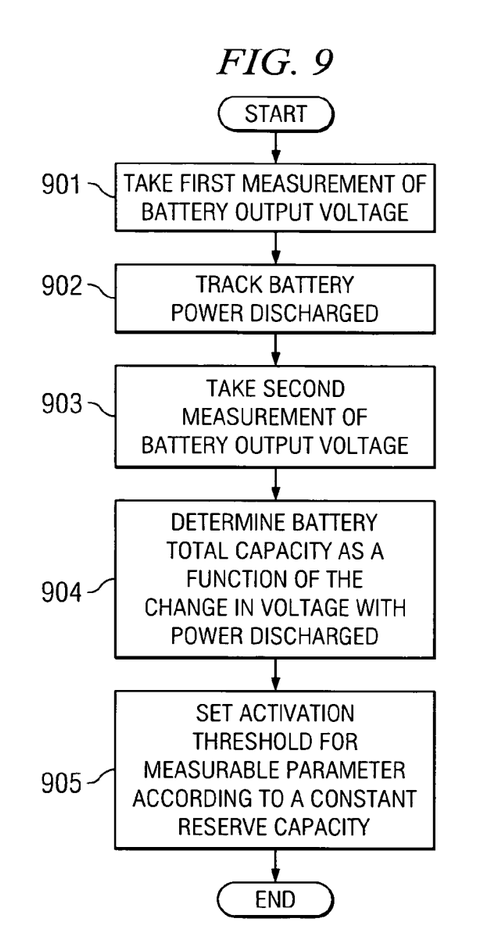
FIG. 9 shows a flow diagram of a method of reserving a constant battery reserve capacity using a battery's change in output voltage based on the known discharge of power.

FIG. 9 shows a method of reserving a constant battery reserve capacity using a battery's change in output voltage based on the known discharge of power. In step 901, a battery's no-load voltage may be measured at the beginning of a discharge period. In step 902, the total discharged battery power may be measured by monitoring discharge voltage, current, and time of discharge. In step 903, at the end of a discharge period, a second no-load voltage may be measured. In step 904, the change in the output voltage based on power discharged from the battery may be used to determine a battery's total capacity. In step 905, a reserve capacity activation threshold for a measurable parameter may be set corresponding to a desired constant reserve capacity. This method may be employed in embodiments using both single-use and rechargeable batteries. In some embodiments, a battery's total capacity may not be determined before setting an activation threshold.

Embodiments of the present invention using a battery total capacity calculation method based on change in battery output voltage during charge or discharge may use a second method of calculation to verify battery total capacity if the change in output voltage is very small, as would occur if an embodiment were discharged or charged for only a short period of time. In this event, for example, an embodiment may use a table to calculate the battery total capacity based on battery output voltage (such as the table discussed above which correlates recharge cycles, time in service, et cetera with total capacity and output voltage), in addition to a method of measuring the change in voltage.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. An implantable pulse generator for generating electrical pulses for stimulating tissue of a patient, the implantable pulse generator comprising:
   pulse generating circuitry for generating electrical pulses;
   communication circuitry for communicating with an external controller
   a rechargeable battery for powering the implantable pulse generator, the rechargeable battery subject to capacity degradation when a voltage of the rechargeable battery falls below a first voltage level;
   charging circuitry for recharging the rechargeable battery by converting RF power into charging current;
   circuitry for monitoring one or more states of the rechargeable battery;
   control circuitry for controlling the implantable pulse generator, the control circuitry controlling the pulse generating circuitry according to one or more parameters;
   wherein the control circuitry, using the circuitry for monitoring, calculates a reserve threshold value indicative of an amount of time remaining until the voltage of the rechargeable battery will reach the first voltage level, the control circuitry calculating the threshold value, in part, by compensating for loss of capacity of the rechargeable battery to maintain a substantially constant reserve over a life of the implantable pulse generator;
   wherein the control circuitry communicates, using the communication circuitry, a signal to the external controller indicating the rechargeable battery should be recharged when the calculated reserve threshold value falls below a predetermined amount.

2. The implantable pulse generator of claim 1 wherein the control circuitry comprises a processor and software code executable by the processor.

3. The implantable pulse generator of claim 1 wherein the control circuitry calculates the reserve threshold value by compensating for prior power usage of the implantable pulse generator by the patient.

4. The implantable pulse generator of claim 1 wherein the control circuitry compensates for loss of capacity of the rechargeable battery by using the circuitry for monitoring to monitor resistance of the rechargeable battery during recharging operations.

5. The implantable pulse generator of claim 1 wherein the control circuitry compensates for loss of capacity of the rechargeable battery by determining an age of the rechargeable battery.

6. The implantable pulse generator of claim 1 wherein the control circuitry compensates for loss of capacity of the rechargeable battery by retrieving a value indicative of a number of recharge cycles applied to the rechargeable battery.

7. The implantable pulse generator of claim 1 wherein the reserve threshold value is a second voltage level.

8. The implantable pulse generator of claim 1 wherein the control circuitry is further operable to modify one or more pulse parameters to reduce a power consumption of pulses generated by the pulse generating circuitry when a voltage of the rechargeable battery reaches a second voltage level, the second voltage level being greater than the first voltage level.

9. A method of operating an implantable pulse generator for generating electrical pulses for stimulating tissue of a patient, the implantable pulse generator comprising:
   powering the implantable pulse generator using a rechargeable battery, the rechargeable battery subject to capacity degradation when a voltage of the rechargeable battery falls below a first voltage level;

generating stimulation pulses by pulse generating circuitry of the implantable pulse generator for delivery to tissue of the patient;

monitoring one or more states of the rechargeable battery;

calculating a reserve threshold value indicative of an amount of time remaining until the voltage of the rechargeable battery will reach the first voltage level, wherein calculation of the reserve threshold value compensates for loss of capacity of the rechargeable battery to maintain a substantially constant reserve over a life of the implantable pulse generator;

communicating a signal to an external controller device indicating the rechargeable battery should be recharged when the calculated reserve threshold value falls below a predetermined amount.

10. The method of claim 9 wherein the calculating further compensates the reserve threshold value for prior power usage of the implantable pulse generator by the patient.

11. The method of claim 9 wherein the calculating compensates for loss of capacity of the rechargeable battery using resistance of the rechargeable battery during recharging operations.

12. The method of claim 9 wherein the calculating compensates for loss of capacity of the rechargeable battery using an age of the rechargeable battery.

13. The method of claim 9 wherein the calculating compensates for loss of capacity of the rechargeable battery by retrieving a value indicative of a number of recharge cycles applied to the rechargeable battery.

14. The method of claim 9 wherein the threshold value is a second voltage level.

15. The method of claim 9 further comprising:

modifying one or more pulse parameters to reduce a power consumption of pulses generated by the pulse generating circuitry when a voltage of the rechargeable battery reaches a second voltage level, the second voltage level being greater than the first voltage level.

* * * * *